(12) United States Patent
Alshemari

(10) Patent No.: US 8,535,348 B1  
(45) Date of Patent: Sep. 17, 2013

(54) SURGICAL NEEDLE HOLDER

(71) Applicant: Hasan M. Sh. Sh. Alshemari, Saad Al Abdulla (KW)

(72) Inventor: Hasan M. Sh. Sh. Alshemari, Saad Al Abdulla (KW)

( * ) Notice: Subject to any disclaimer, the term of this patent is extended or adjusted under 35 U.S.C. 154(b) by 0 days.

(21) Appl. No.: 13/685,580

(22) Filed: Nov. 26, 2012

(51) Int. Cl.  
*A61B 17/00* (2006.01)

(52) U.S. Cl.  
USPC .......................... 606/208; 606/147

(58) Field of Classification Search  
USPC .................. 606/144–148, 205–211; 81/349, 81/383.5, 416  
See application file for complete search history.

(56) References Cited

U.S. PATENT DOCUMENTS

| | | | |
|---|---|---|---|
| 4,572,185 A * | 2/1986 | Rich | 606/145 |
| 6,017,358 A | 1/2000 | Yoon et al. | |
| 7,470,278 B2 | 12/2008 | Frank | |
| 7,947,052 B2 | 5/2011 | Baxter, III et al. | |

* cited by examiner

*Primary Examiner* — Thomas McEvoy  
(74) *Attorney, Agent, or Firm* — Richard C. Litman

(57) ABSTRACT

The surgical needle holder includes two elongated arms having scissor finger loops on one end and a pair of needle gripping jaws on the opposite end. The elongated arms are pivotally attached to each other. A first jaw is pivotally mounted via an actuator rod interconnecting the first jaw to one of the arms, opening and closing with respect to the second jaw as the elongated arms pivot with respect to each other. The jaws are designed to grip a surgical needle when in the closed position. Ratchet lock members attached to the elongated arms lock the jaws in the closed position in a manner similar to the locking of a hemostat. Mechanical configuration of the needle holder allows motion of the needles to be along any plane parallel to the longitudinal axle of the device while the surgeon's hand is in a neutral position.

3 Claims, 5 Drawing Sheets

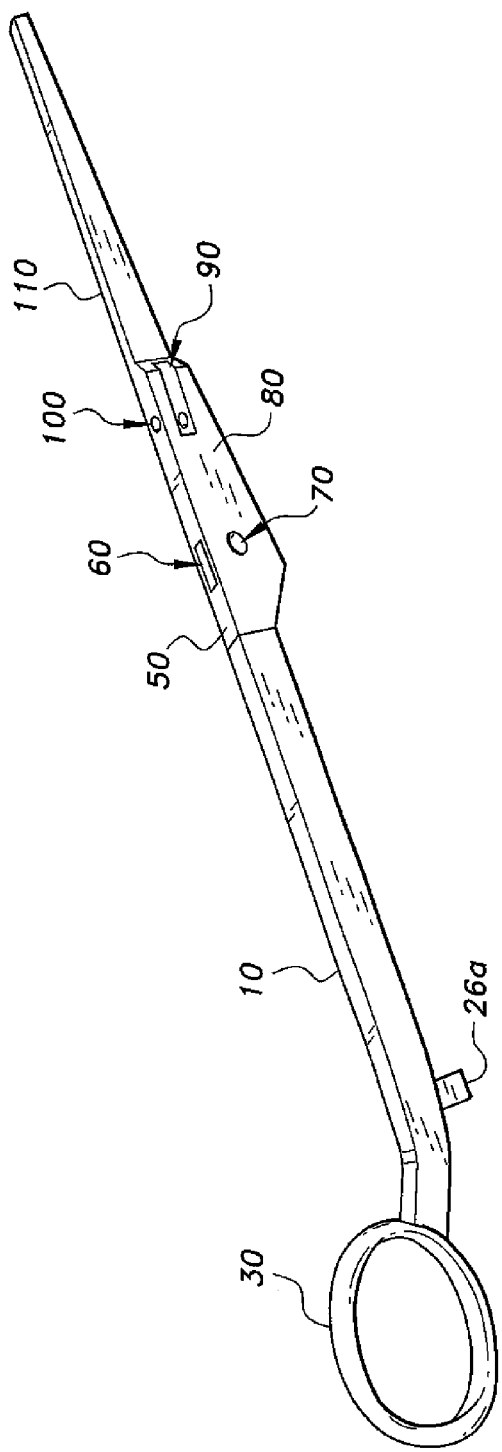
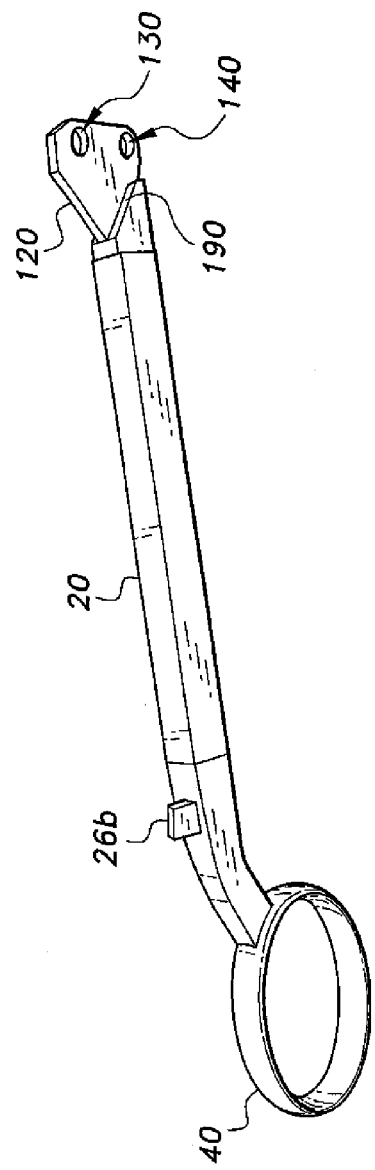

SURGICAL NEEDLE HOLDER

BACKGROUND OF THE INVENTION

1. Field of the Invention

The present invention relates generally to surgical instruments, and more particularly to a surgical needle holder that provides a holding and driving instrument for a suture needle.

2. Description of the Related Art

A needle holder, also called a needle driver, is a surgical instrument similar to a hemostat that is used by doctors and surgeons to hold a suturing needle for closing wounds during suturing and surgical procedures. The surgical needle holder assists the surgeon in perforating the tissue and creating the tracts at a desired depth. The surgical needle holder is configured to hold the needles securely when creating the tracts, and is also configured to disengage from the needles after the tracts have been created. It is common surgical practice for a physician to join various tissues by passing a needle with attached suture through the tissue. The suture is then tied to approximate the tissues.

The parts of a simple needle holder are the jaws, the joint and the handles. Most needle holders also have a clamp mechanism that locks the needle in place, allowing the user to maneuver the needle through various tissues. To maintain a firm grip on the needle, the jaws are often textured and short compared to the handles, thereby increasing the applied force via the lever principle. With the simple needle holder, the handle portion and the jaws portion work together in-plane. One particular problem arises when the surgeon, from an ergonomic standpoint, needs to operate the jaws with his/her hand rotated 90° from the jaws action.

Thus, a surgical needle holder solving the aforementioned problems is desired.

SUMMARY OF THE INVENTION

The surgical needle holder has two elongated arms that end in expansions in the form of scissor finger loops for introducing the fingers and correspondingly actuating both arms. The elongated arms are pivotally attached to each other. The distal end of one of the arms forms a fixed jaw. The other arm is shorter, and is linked to a pivotally mounted jaw by an actuator rod. The arms are connected so that pivoting the finger loops away from each other causes the pivotally mounted jaw to pivot away from the fixed jaw in a plane orthogonal to the plane of the finger loops, and pivoting the finger loops towards each other causes the pivotally mounted jaw to close against the fixed jaw in order to grip a needle between the jaws.

The needle holder has ratchet lock members extending towards each other between the elongated arms in order to lock the jaws on the surgical needle, similar to the locking of a hemostat, thereby clamping the needle between the jaws. The needle holder is preferably constructed of surgical stainless steel.

The surgical needle holder is configured in such a manner as to manipulate and move needles along any plane parallel to the longitudinal axis of the device. By using two perpendicular pivot planes in a single side rod system, the related needle is grasped in a position to function while the operator's hand is in neutral position. In such an embodiment, the needle automatically moves into an ideal position for straight vertical motion, rather than elliptical motion. In other words, the needle is in a position to enter the tissue without any hand motion.

This provides the surgeon with an implement to facilitate driving a needle suture in difficult conditions of long reaching tissues or limited space, such as when reaching down into the abdomen or into the base of tongue, during which the surgeon is required to handle and manipulate these instruments in relatively small and sometimes minute increments and degrees. The single side rod system configuration in the needle holder will add more control of a suturing operation by increasing comfort to the surgeon, steadiness of the surgeon's hand, and accuracy in the exact points of penetration.

These and other features of the present invention will become readily apparent upon further review of the following specification and drawings.

BRIEF DESCRIPTION OF THE DRAWINGS

FIG. 3 is a perspective view of the upper arm of the surgical needle holder of FIG. 1.

FIG. 4 is a perspective view of the lower arm of the surgical needle holder of FIG. 1.

Similar reference characters denote corresponding features consistently throughout the attached drawings.

DETAILED DESCRIPTION OF THE PREFERRED EMBODIMENTS

Figure 1:
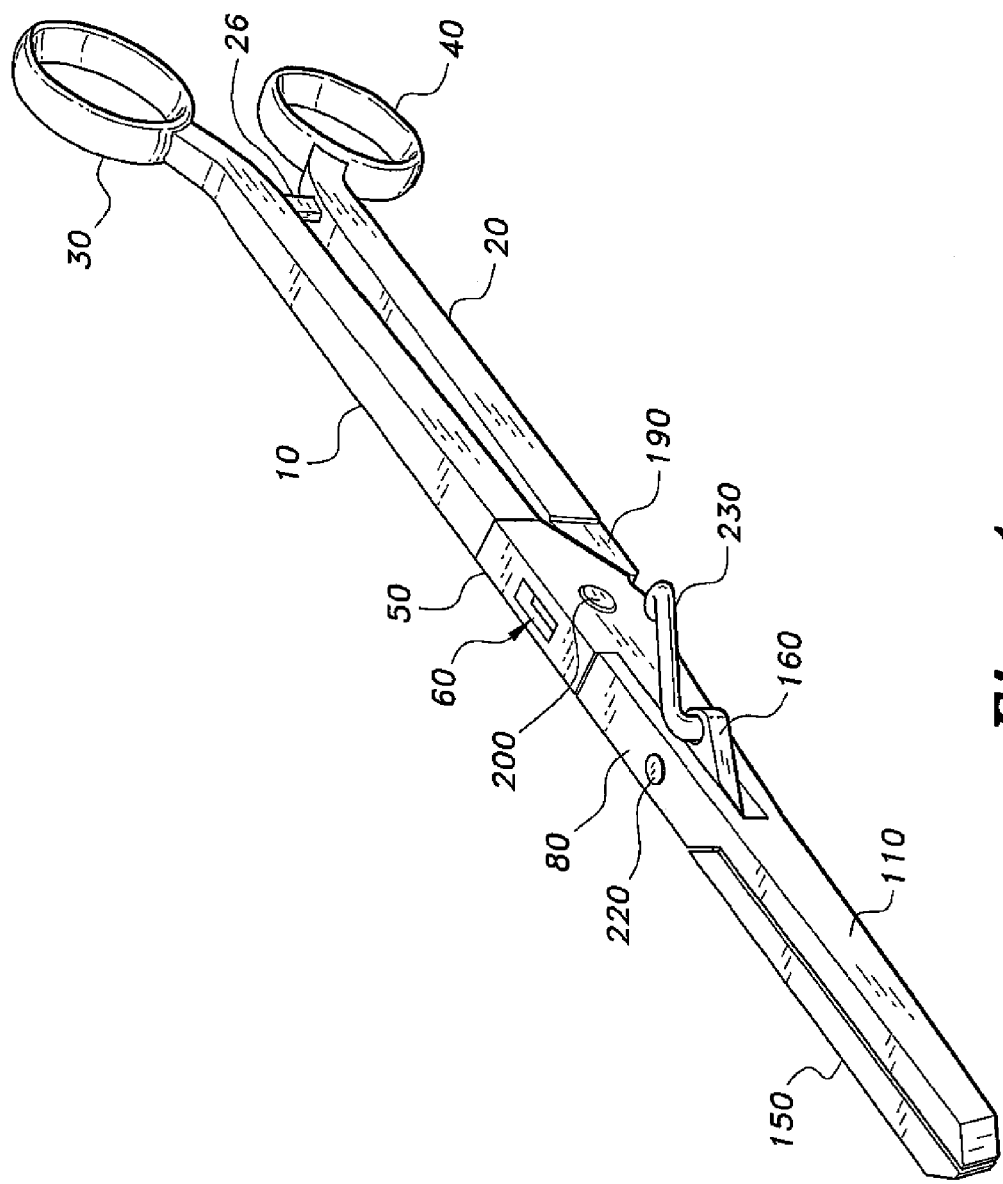
FIG. 1 is a perspective view of a surgical needle holder according to the present invention, shown in a closed position.
Figure 2:
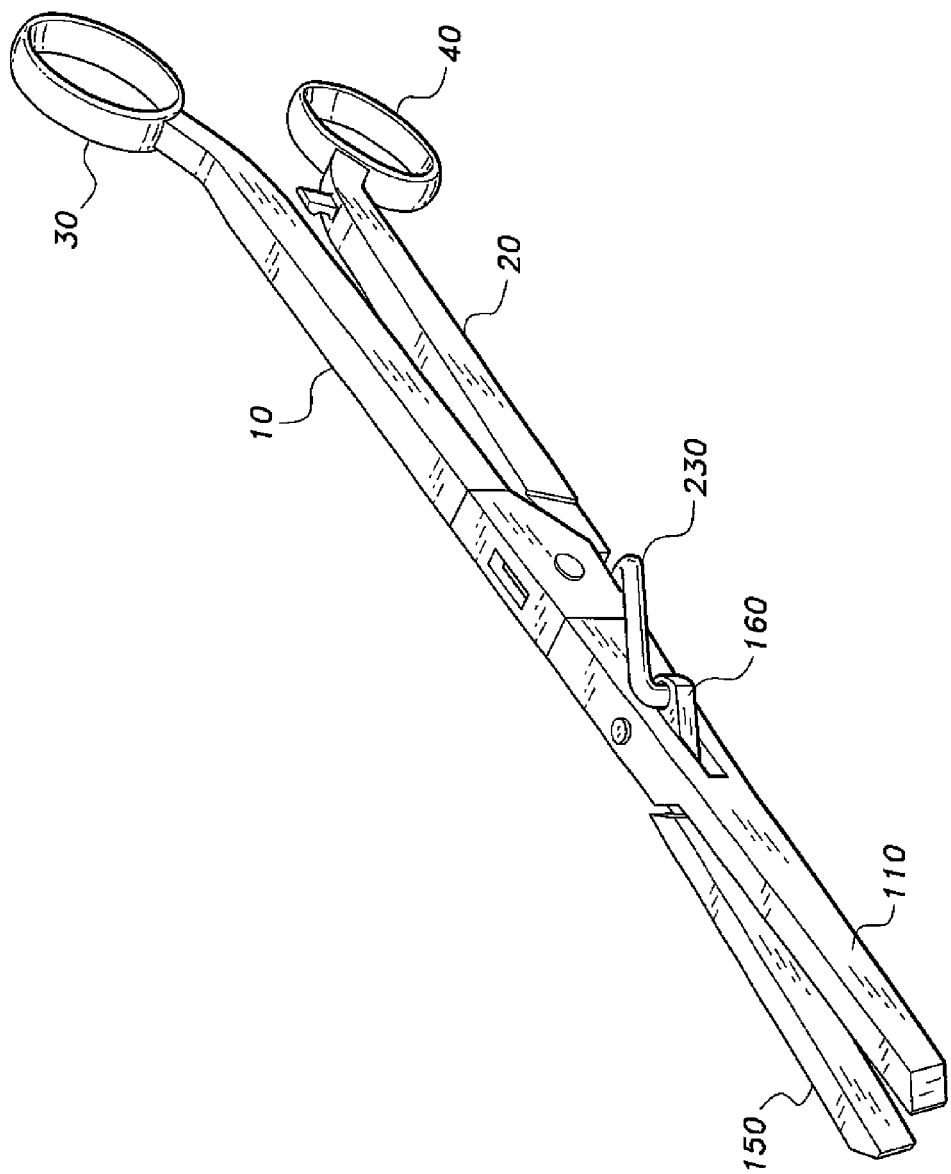
FIG. 2 is a perspective view of the surgical needle holder of FIG. 1, shown with the jaws in an open position.

As shown in FIG. 1, the surgical needle holder comprises an upper elongate scissor arm 10 and a lower elongate scissor arms 20 pivotally attached to each other and extending on one end to form upper and lower scissor finger loops 30 and 40, respectively. The finger loops 30 and 40 are adapted for a user introducing fingers to manipulate the arms 10 and 20. The pivotally attached scissor arms 10 and 20 are in operable communication with the needle gripping jaws 110 and 150 to provide pivotal opening and closing of the needle gripping jaws 150 and 110 as the arms 10 and 20 are pivoted. Pivot action of the jaws 150 and 110 are in a plane which is 90° from the pivot plane of the scissor thins 10 and 20. FIG. 2 shows the device where the needle holding jaws 110 and 150 are open.

As shown in FIGS. 1-4, the upper arm 10 is of unitary construction extending from the finger loop 30 proximally to the stationary gripper jaw 110 distally. The stationary gripper jaw 110 tapers down to a needle-nosed point most distal from the finger loop 30. Disposed between the opposing distal and proximal ends of the upper arm 10 is a fulcrum attachment member 50 that is vertically slotted and has a horizontally disposed pivot bore 70 through the vertically slotted portion 60 for attachment of the lower arm 20. An extension 80 from the vertically slotted portion 60 of the fulcrum attachment member 50 extends into a horizontally slotted portion 90, which has vertically disposed pivot bore for pivotal attachment of the pivotal needle gripping jaw 150.

As most clearly shown in FIG. 4, the lower arm 20 is also of unitary construction, extending from the finger loop 30 proximally to a planar attachment member 120 distally. The planar attachment member 120 has a polygonal shape, having an apical portion joined to a tapered region 190 of the lower arm 20. A lower bore 140 and an upper bore 130 are disposed in vertical alignment on the planar attachment member 120, near the edge of the planar attachment member 120 opposing its apical portion.

Figure 5:
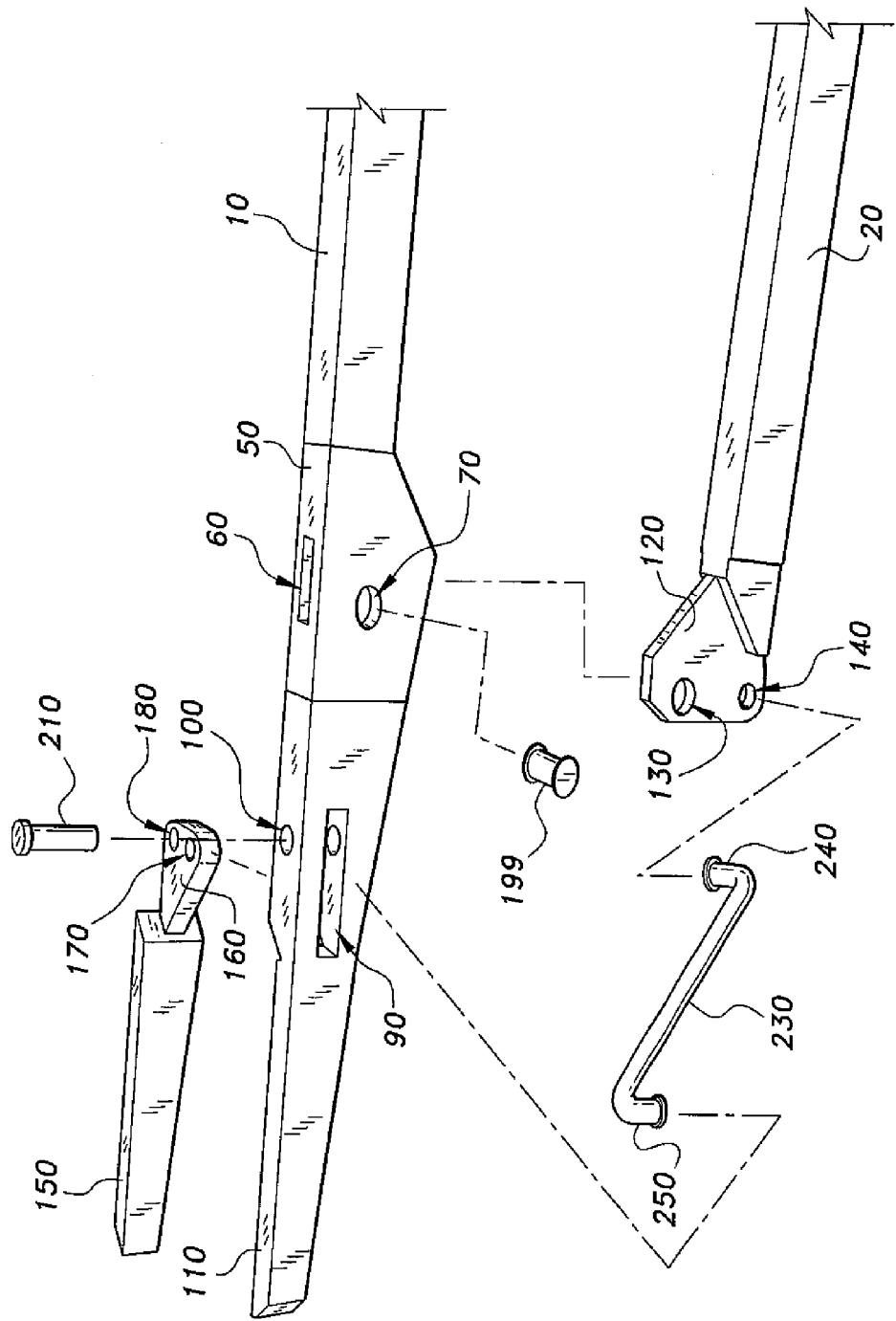
FIG. 5 is an exploded partial perspective view of the surgical needle holder of FIG. 1, showing pivotal attachment of the arms to each other and attachment of the pivotally mounted jaw to the arms.
Figure 6:
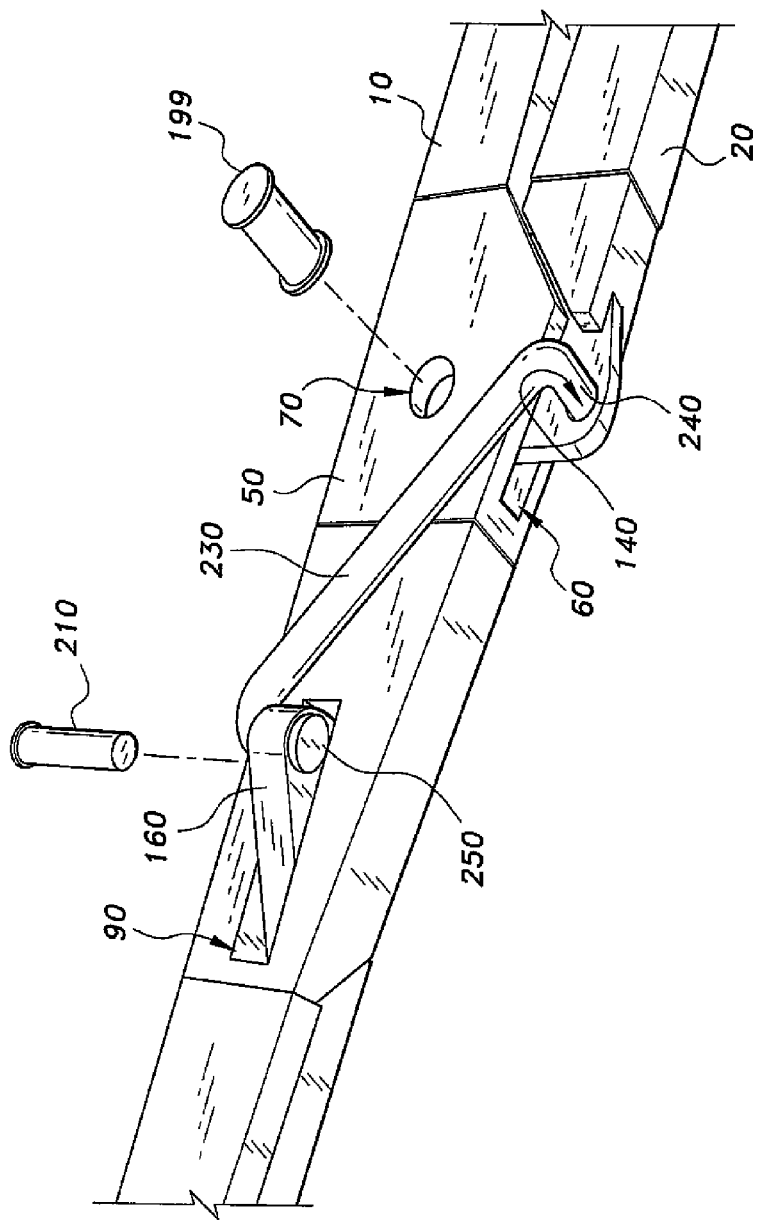
FIG. 6 is a partial perspective view of the surgical needle holder of FIG. 1, showing pivot pins exploded away from the holder.

As shown in FIG. 5, the upper bore 130 of the planar attachment member 120 is aligned with the horizontally disposed pivot bore 70 of the fulcrum attachment member 50 and fastened by a pivot pin 199 (which may be a rivet) disposed through the bores 130 and 70. This arrangement pivotally attaches the upper arm 10 to the lower arm 20 and allows the planar attachment member portion 120, which includes the lower bore 140, to extend below the slot 160 and pivotally move forward and backward as the arms 10 and 20 are positioned away or towards each other. As most clearly shown in FIG. 5, the pivotal gripper jaw 150 is tapered end to end. A horizontally extending planar attachment cam 160 is attached to and extends from the thickest end of tapered gripper jaw 150. A wide lobe portion of the cam 160 opposes the narrow attachment end of the cam 160 to jaw 150, and has two bores 170 and 180 disposed in horizontal alignment with each other. The cam 160 is disposed through the horizontal slot 90 in the upper arm 10, and the cam's bore 180 is placed in alignment with bore 100, which extends vertically through the slot 90. A pivot pin 210 is disposed through the bores 180 and 100, and pivotally attaches the cam 160 to the upper arm 10 with the cam bore 170 extending to the opposite side of the slot 90 from the jaw 150. Due to the eccentric shape of the cam 160, a forward pivotal motion of bore 170 causes the cam 160 to pivot the gripper jaw 150 away from gripper jaw 110, and a backward pivotal motion of bore 170 causes the cam 160 to pivot the gripper jaw 150 towards the fixed or stationary gripper jaw 110. An elongate actuator rod 230 has a horizontal bend at end 240 and a vertical bend at end 250. The horizontal end 240 of the actuator rod 230 extends through bore 140 to pivotally attach the rod 230 to the planar attachment member 120, and the vertical end 250 extends through bore 170 to pivotally attach the rod 230 to the cam 160, thereby linking pivotal motion of the arms 10 and 20 to pivotal opening and closing of the pivotal gripper jaw 150 from stationary gripper jaw 110. FIG. 6 shows a detailed perspective view of the cam actuator 230 coupled to the cam 160 of pivotal gripper jaw 150 and to the planar attachment member 120 of the lower arm 20.

A conventional locking ratchet 26a, 26b is attached to the elongate arms 10 and 20, respectively, near the finger grips 30 and 40. The ratchet mechanism 26a and 26b has a detent mechanism that can lock the arms 10 and 20 in a user-desired pivotal configuration. The ratchet members 26a and 26b includes a detent mechanism, which comprises matching notches or splines on opposing surfaces of the members, which engage one another, thereby locking as the finger loops 30 and 40 are brought together.

The present needle holder is preferably constructed of surgical stainless steel. As shown in FIGS. 1 and 2, the surgical needle holder can be adjusted to a fully closed position or to a fully open position. Moreover, the ratcheting mechanism provided by ratchet members 26a, and 26b, in combination with cam actuation of the rod assembly 230, allows the needle holder to be adjusted to any position in-between fully open and fully closed.

The tapered design of the jaws 110 and 150 forms a pointed tip, which allows for good directional placement and visualization of needle position by the surgeon using the surgical needle holder. The gripping surface of the jaws 110 and 150 are crosshatched, grooved, or knurled to ensure positive engagement with a curved surgical needle.

The finger loops 30 and 40 and the elongated arms 10 and 20 allow the surgeon to grasp the instrument and apply pressure to close or open the mobile or pivotal jaw 150. When the arms 10 and 20 are extended apart at the finger grips 30, 40, the lower (in the drawing) arm 20 will cause the vertical extension of the lower arm 120 to move in downward motion. This will transmit motion to the mobile gripper jaw 150 to move clockwise in order to open laterally at the pivot pin 210.

The rod 230 is capable of movement in a forward and backward direction with respect to the reciprocal movement of the lower elongated arm 20 at the pivot axis secured by pin 200. This configuration allows the mobile gripper jaw 150 to rotate in reciprocal movement in clockwise and counterclockwise direction at the pivot axis secured by pin 200.

In other words, the mobile jaw member 150 can move toward and/or away from the other non-mobile jaw 110. By applying the configuration of actuator rod 230, the motion of needles will be along any plane parallel to the longitudinal axis of the surgical tool.

It is to be understood that the present invention is not limited to the embodiments described above, but encompasses any and all embodiments within the scope of the following claims.

I claim:

1. A surgical needle holder, comprising:
 a first elongate arm having a first annular finger grip at one end, said first elongate arm extending into a stationary first gripper jaw at a distal end opposite the finger grip;
 a fulcrum attachment member disposed between the opposing distal and finger grip ends of the first elongate arm;
 a vertical slot disposed in said fulcrum attachment member;
 horizontally aligned pivot through-bores disposed through the vertically slotted portion of said fulcrum attachment member;
 an extension of said fulcrum attachment member forming a horizontally disposed slotted portion;
 vertically aligned pivot through-bores disposed through said horizontally disposed slotted portion of said fulcrum attachment member;
 a second elongate arm having a second annular finger grip at one end, said second elongate arm extending into a planar attachment member at a distal end opposite the finger grip, said planar attachment member having a polygonal shape with an apical portion joined to a tapered region of the second elongate arm;
 lower and upper through-bores disposed in vertical alignment on the planar attachment member near an edge of the planar attachment member opposing its apical portion, the upper through-bore of the planar attachment member being in alignment with the horizontally aligned pivot through-bores of the fulcrum attachment member;
 a fastening pin disposed through said upper through-bore and said horizontally aligned pivot through-bores to pivotally fasten said first and second elongate arms to each other, portion of said planar attachment member that includes said lower through-bore being exposed, extending below said vertical slot of said fulcrum attachment member;
 a second gripper jaw tapering from a proximal thick end to a distal narrow end, shape of said second gripper jaw substantially and complementarily matching shape of said first gripper jaw;
 a horizontally extending planar attachment cam, a narrow portion thereof attaching said cam to said thick end of said second gripper jaw, a wide lobe portion of said cam opposing said narrow cam portion, first and second cam through-bores disposed in horizontal alignment near an edge of said wide lobe cam portion, said cam being disposed through a horizontal slot of said horizontally slotted portion placing said first cam through-bore in alignment with said vertically aligned pivot through-bores in the horizontally slotted portion of the fulcrum attachment member, said second cam through-bore being exposed through the horizontal slot;

a fastening pin disposed through said first cam through-bore and said vertically aligned pivot through-bores to pivotally fasten said second gripper jaw with respect to said first gripper jaw; and an elongate actuator rod having a horizontal bend at a first end and a vertical bend at a second end, the first end being pivotally attached to said exposed lower-through-bore of said planar attachment member, said second end being pivotally attached to said exposed second bore of said cam thereby linking pivotal motion of said arms to pivotal opening and closing of said pivotal second gripper jaw with respect to said stationary first gripper jaw, said arm pivotal motion being displaced by 90° from said gripper jaw pivotal motion.

2. The surgical needle holder according to claim 1, further comprising first and second ratchet lock members attached to and extending from said first and second elongate arms, respectively, the ratchet lock members engaging each other to form a ratchet lock when the finger grips are pivoted towards each other in order to lock the surgical needle between the gripping jaws.

3. The surgical needle holder according to claim 1, wherein each said gripping jaw has a gripping surface having a cross-hatched gripping pattern disposed on the gripping surface in order to firmly grip the surgical needle between the gripping jaws.

\* \* \* \* \*